(12) United States Patent
Malodobry

(10) Patent No.: US 7,314,470 B2
(45) Date of Patent: Jan. 1, 2008

(54) SCAR-FREE REMOVAL OF TATTOOS

(76) Inventor: Wolfgang Malodobry, Oststrasse 4, D-53879, Euskirchen (DE)

(*) Notice: Subject to any disclaimer, the term of this patent is extended or adjusted under 35 U.S.C. 154(b) by 593 days.

(21) Appl. No.: 10/362,594

(22) PCT Filed: Sep. 11, 2001

(86) PCT No.: PCT/EP01/10531

§ 371 (c)(1),
(2), (4) Date: Feb. 24, 2003

(87) PCT Pub. No.: WO02/36027

PCT Pub. Date: May 10, 2002

(65) Prior Publication Data

US 2004/0111107 A1    Jun. 10, 2004

(30) Foreign Application Priority Data

Nov. 4, 2000  (DE) ................. 100 54 718
Nov. 4, 2000  (DE) ................. 200 18 848 U
Nov. 13, 2000 (DE) ................. 100 56 114

(51) Int. Cl.
*A61B 17/50*  (2006.01)

(52) U.S. Cl. .................. 606/131; 128/898
(58) Field of Classification Search .......... 606/9, 606/11, 131, 186, 1; 106/31.01, 31.03, 31.33, 106/31.02, 31.64
See application file for complete search history.

(56) References Cited

U.S. PATENT DOCUMENTS

| | | | |
|---|---|---|---|
| 3,589,363 A | 6/1971 | Banko | |
| 5,000,752 A | 3/1991 | Hoskin et al. | |
| 5,833,649 A | 11/1998 | Atef | |
| 5,984,915 A | 11/1999 | Loeb et al. | |
| 6,192,890 B1 * | 2/2001 | Levy et al. | 128/899 |
| 6,749,602 B2 * | 6/2004 | Sierra et al. | 606/9 |
| 6,881,249 B2 * | 4/2005 | Anderson et al. | 106/31.03 |

FOREIGN PATENT DOCUMENTS

DE    43 08 824 C1    5/1994

OTHER PUBLICATIONS

Fielder, Lexikon der Hilfsstoffe für Pharmazie, Kosmetik und angrensende Gebiete, 4$^{th}$ Edition, 1996.

* cited by examiner

*Primary Examiner*—Kevin T. Truong
(74) *Attorney, Agent, or Firm*—Venable LLP; Thomas G. Wiseman

(57) ABSTRACT

A method for scarless removal of a tattoo from skin which is one of human or animal skin includes pricking at least one needle through a surface of the skin essentially perpendicular thereto into the tattoo comprised of agglomerates of pigment comprising at least one of inorganic and organic color pigments present in the skin, whereby the agglomerates are mechanically destroyed; and one of applying skin irritants to the skin surface or introducing skin irritants into the agglomerates at least one of before, during or after mechanical destruction.

6 Claims, No Drawings

SCAR-FREE REMOVAL OF TATTOOS

BACKGROUND OF THE INVENTION

1. Field of the Invention

The invention relates to the scarless removal (which does not mean melanin scars) of non-natural tattooed color pigments in the human or animal skin.

2. Description of the Related Art

In modern tattooing, the ink (which hereinafter means the tattoo inks) is injected into the skin with a machine tool. In professional tattooing, the ink is injected into the skin by the uniformly running gun. The skin is constituted by 3 different layers:
1. Epidermis
2. Dermis
3. Hypodermis The epidermis is about 0.5 mm thick and is further subdivided into different layers.

The outermost thereof is the horny layer (stratum corneum) which is about 10 to 20 cell layers (0.015 mm) thick. Its dead and cornified cells are constantly cast off outwards and thus must be replaced by the cell production in the germ layer. This transition is effected by the cells' closing up and flattening, disintegration of their nuclei and inclusion of keratin grains in their protoplasm. The thus formed grain layer, at thick skin regions, changes into the stratum lucidum to form a highly light-refracting mass by a cross-linking of the keratin grains and formation of fibrous structures, and finally changes into the horny layer.

The dermis is formed by the mesoblast. It consists of connective tissue and contains vessels and nerves, and even muscles in some places. The filled state of the capillary vessels contained in the dermis causes the pink tinting of the skin. The reticular dermis (stratum reticulare) contains the sweat glands and the larger vessels and nerves. Tattooing involves injecting the ink into the dermis about 1 to 1.5 mm deep.

Beneath the dermis lies the hypodermis. Embedded therein, the subcutaneous fatty tissue serves for the heat insulation of the body, as a cushion, and for the storage of compounds.

The ink is poured from the commercial bottle into disposable caps. From these caps, the tattooist withdraws the ink with the gun during the injection. The gun itself is provided with freshly disinfected needles and handle pieces for each client. The area to be tattooed is shaved with a disposable razor, cleaned with a disinfectant and moistened. The area is shaved lest hair should be punched under the skin with the needles. This could result in infections or inflammations. When the color is being changed and after the gun has been used, the needle and often also the handle piece are cleaned.

There is no tank on the machine, but the needle is dipped at regular intervals into the (disposable) cap with the ink. If the ink is injected too deep, the color will blur under the skin (so-called blow-out). If the ink has not penetrated deep enough, the color will blur, the color may grow pale in the course of time. For the machines, different heads for different purposes exist. Fine outlines are usually pricked with a head bearing several, especially 3 or 5, needles with 0.25 to 0.40 mm diameter, while solid areas are pricked with as much as 10 to 14 needles simultaneously. These needles are prepared manually from surgical steel (Nirosta® or V2A) and examined for damage on the tip with a microscope prior to use. The needles are then bunched according to need either by the tattooist himself or by a supplier, and soldered to a support with a special solder metal. Thus, the needle combination can be selected according to the tattooist's desires.

In practice, only electric machines are employed. In contrast to previous methods, this method is relatively low-pain and is well suitable for fine pictures due to the uniform vibrations. The tattoo gun can be wielded by the tattooist almost like a painter's brush. The device functions like an electric door bell with a needle connected thereto. At the head of the machine, there are one or two magnet coils which are activated by supplying current. The metal spring positioned above the coils is attracted by the coils, bent downwards and thereby moves the connected needle. While the metal spring is being pulled downwards, it interrupts the circuit, and the magnet coils are again switched off, and the spring will swing upwards again. In the up position, it again closes the circuit, and the same cycle begins from the start. The needles connected to the spring are thereby moved up and down. Some tattooists increase the tension of the spring by additionally stretching rubber bands around the gun.

The fact that the pricking frequency is kept constant thereby enables a uniform pressure and constant color injection. The speed, which is adjusted at the machine's power supply, is usually between 30 and 40 pricks per second.

For removing tattoos, there are different methods:

One relatively wide-spread method for making a tattoo disappear is the "cover up" method. Thus, the old picture is integrated into a new picture and supertattooed.

The known beginning of tattoo removal is somewhere at the time around 54 after Christ. A Greek physician had developed a chemical method which led to necrosis of the pricked skin tissue. A mixture of garlic, onions and cantharidin served this purpose. This is a secretion of a beetle's gland. This paste was coated onto the skin to achieve the desired effect.

Simply cutting out the tattoo is not recommendable. In this method, the concerned area is removed by surgery or punching and sewn. This method can only be used for smaller tattoos, but usually leads to unsightly scars even with such minor operations.

In contrast, a very rough method is the mechanical method, the so-called dermal abrasion, in which the skin is simply sliced off or abraded. This naturally produces scars. Often, pigments which lie in different skin layers are not removed along with the others. In addition to the scar, a dark shade from the remnants of the tattoo showing through remains.

Another method involves the tangential excision and covering with a "split-skin graft". The skin layer concerned is cut out under general anesthesia while it is tried to save as much as possible from the underlying skin layer. The open area is covered with split skin and saved from unnecessary scar formation over months by compression bandages, and adapted to the environment.

The removal of tattoos using a laser has become established in the meantime, as described, for example, in U.S. Pat. No. 5,984,915 or U.S. Pat. No. 5,000,752.

However, this clean treatment with its relatively simple handling is not perfect either. The treatments are usually expensive and last rather long until an acceptable result has been achieved.

The laser treatment utilizes the principle of light reflection by the pigment particles. Tattoos are known to involve inorganic or organic color pigments which are deposited in the skin in the form of agglomerates. Especially in the dermis, these pigments are deposited permanently since they are not separated and extracted by the immune system.

The visible tattoo represents the light reflection by the pigment particles in their inherent wavelength of light. Now, when such agglomerates are irradiated with their very own "wavelength" by a high-energy laser, they will absorb the radiation, are destroyed, and the remnants are transported off by the defense system as foreign matter. The surrounding skin tissue is supposed to not respond to this wavelength of the laser and thus remain undamaged.

After the treatment, the area concerned is somewhat lighter than the surrounding areas, but this is regulated and, after some time, adjusted by the natural pigment formation of the skin.

Now, the number and duration of the laser treatments depends on a number of factors:

the size of the tattoo;
its depth;
color;
condition and strength of the immune system;
regularity of the treatments;
aftertreatments;
quality of the tattoo.

The quality plays a critical role since, with manual pricks, the color pigments reside in skin layers of different depths and are irregularly distributed, whereas machine-pricked pictures should be regularly within one skin layer.

For non-professional tattoos (unicolored, blue-black) of a size of 10×10 cm, from 4 to 8 sessions, and for a professional tattoo (multicolored), from 8 to 12 sessions are expected. Each session is cost-intensive.

One of the newest treatments is the so-called diathermy. It does not utilize the wavelength property of the color, but relies on a thermal treatment of the skin. By high-frequency electric currents, electric energy is transformed into heat energy within the skin. Depending on the power, this results in a boiling or evaporating of the cell fluid. The cells die therefrom. The technique is similar to that of the pricking itself. Namely, the pricking of the needles destroys the uppermost skin cells, and the color pigments are deposited in the intact cells. Now, in the treatment with the corresponding diathermy equipment, these cells, which are still intact, are destroyed, not mechanically, but by heat. The liquid cell substance evaporates, and the included color pigments are cast off together with the dead cells. Due to the low current, there is no danger to the remaining skin. Reportedly, no scars remain. This killing and damaging of the skin by the action of heat stimulates the process of cell division. Because of the injury, the skin tries to heal itself. The dead colored skin is only shifted outwards for healthy skin to grow in its place from beneath. After some time, this typical scab layer, which now contains the color pigments, forms on the skin. The advantage of this method over the laser method is supposed to reside in the fact that all color regions are covered equally, and the individual color regions need not be attacked separately by modulating the wavelength. The color pigments are not destroyed thereby. The duration and costs are highly dependent on the expense and duration of the treatment. The skin is treated virtually layer by layer, which can be lengthy especially for old and intensely colored tattoos. For old and deep tattoos, a number treatments of from 5 to 8 is reported. DE 43 08 824 C1 relates to a corresponding method, but points out that a scar will naturally form after the scab layer has fallen off. It is suggested to remove the scars by abrading the skin.

Water-jet cutting is a method which is normally used for the cutting of fabrics. A fine water jet which can be changed in terms of diameter, pressure and pulse frequency and provided with various additions flushes the color pigments away from under the skin.

In the area concerned, the skin is incised and lifted off in order that the color pigments are accessible at all. Thus, scars will remain. As in diathermy, it is not important which color pigments are involved. The color pigments do not remain inside the body, but are flushed out. Even large-area tattoos are reported to be no problem. With respect to tattoos, this method is still in a test phase. Nothing is known about the duration and costs of the treatment. However, in view of the fact that a hospital stay is required, the costs will probably be very high.

U.S. Pat. No. 5,833,649 describes a method for masking tattoos in which an existing tattoo is only concealed, but not removed.

Thus, it is the object of the present invention to provide an inexpensive method for the scarless removal of tattoos from the human or animal skin.

SUMMARY OF THE INVENTION

In a first embodiment of the invention, the above object is achieved by a method for the scarless removal of tattoos from the human or animal skin, characterized in that one or more needles are pricked through the skin surface essentially perpendicular thereto into the agglomerates of inorganic and/or organic color pigments present in the skin, whereby the agglomerates are mechanically destroyed, and further that skin irritants are applied to the skin surface and/or introduced into agglomerates before, during or after the mechanical destruction; and

DETAILED DESCRIPTION OF THE INVENTION

According to the present invention, a tattoo is removed by mechanically destroying the relatively large color pigment agglomerates directly on the spot within the dermis. The smaller fragments of the agglomerates formed in the mechanical destruction can then be cast off along with cells in the natural healing process of the skin.

The fact that, according to the present invention, the tool is to penetrate the skin "essentially perpendicular to the skin surface" is only meant to provide a qualitative differentiation from mechanical skin peeling methods in which the top areas are virtually cut off in an essentially tangential direction below the skin surface and, after the tattoo has been removed, are replaced in some cases. Thus, the term "perpendicular to the skin surface" essentially characterized an angle of from 0 to 90°, especially up to 60°, with respect to a vertical on the skin surface.

After the mechanical action, the needles introduced into the color pigment agglomerates are removed from the color pigment agglomerate, but may also be introduced again into the agglomerate for any number of times if necessary. Thus, it is possible to perforate the pigment agglomerate. If possible, the size of the needles should be on the same order or smaller as compared with the color pigment agglomerates. "Needles" within the meaning of the present invention includes, for example, drills or hollow needles for injection or for the sucking of gases or liquids.

"Scarless" within the meaning of the present invention means freedom from scars when observed with the naked eye.

In order to improve the mechanical destruction of the color pigment agglomerates, the needle to be introduced should have a relatively rough or sharp-edged surface. While, in the tattooing itself, the ink is introduced into the cells of the dermis with as smooth as possible a needle having a smooth surface, according to the present invention, when the tattoo is removed, it is particularly preferred to contact the color pigment agglomerates with a rough surface in order that the natural healing process is promoted thereby.

According to the present invention, it is particularly preferred to employ one or more needles for the mechanical destruction of the color pigment agglomerates. These needles can be connected with a tattooing gun in a per se known manner. By treating the skin with an appropriate tattooing gun and appropriate needles, for example, having a diameter of from 0.001 to 0.5 mm, especially from 0.01 to 0.3 mm, it is thus possible to remove tattoos without the formation of scars. Usual tattooing needles have a relatively smooth surface, and therefore, it is particularly preferred according to the present invention to roughen tattooing needles accordingly and employ them. Of course, it is also possible to employ needles which have already been pre-fabricated industrially.

In addition, however, instead of employing the usual ink cap containing an ink for tattooing, for the removal of a tattoo, it is also possible to employ a corresponding attrition agent or abrasive, such as quartz or diamond dust, in order to enhance the mechanical destruction of the color pigment agglomerates.

In a similar manner as in diathermy, the color pigment agglomerates are shifted outwards for healthy skin to grow in their place from beneath, or moved into the hypodermis where they are disposed off by the immune system. In this case too, a typical scab layer which contains color pigments can form on the skin after some time. However, in the treatment according to the invention, no liquid cell substance is evaporated. The vitality of the cell is to be preserved, if possible. Also, surrounding regions outside the color pigment agglomerates are not treated with heat either, so that the full wound healing capability of the skin is available. This is clearly in contrast to diathermy which cannot avoid the burning or scalding of surrounding cells. The substances released thereby cause a high permeability of the surrounding tissues so that blood plasma fluid leaks into the tissue. However, the method according to the invention dispenses with the thermal action and therefore causes virtually no damage to the skin.

The usual wound healing conveys the color pigment agglomerate fragments to the skin surface where they are then scaled off.

According to the present invention, the method is applied in a way which involves the application of so-called skin irritants introduction to the skin surface or the direct introduction thereof into the agglomerates or fragments of the color pigment agglomerates before, during or after the mechanical destruction of the color pigment agglomerates. In "Lexikon der Hilfsstoffe für Pharmazie, Kosmetik und angrenzende Gebiete", 4th Edition, 1996, under the item "Hautirritationen" [skin irritations], Herbert P. Fiedler defines skin irritants as chemical substances which exert an irritant action on the human skin when contacted therewith. Thus, skin irritants within the meaning of the present invention can have a primary irritant action which occurs immediately upon contact with the skin. Less suitable according to the present invention are skin irritants in which a damage becomes manifest only after a prolonged continuous action of the skin-irritant substance in subliminal doses in the form of a degenerative eczema. Thus, it is particularly preferred according to the present invention to employ skin irritants which serve as skin-irritating agents.

Fiedler (supra) defines a scale, which is officially acknowledged in the U.S.A., for testing a skin-irritant effect. The most strongly skin-irritant substances are designated as corrosive and highly dangerous and must be accompanied by a warning. Such skin irritants will hardly be employed for the present invention, at any rate, not in a pure form. The same applies to primary skin irritants, which are also highly dangerous and must bear warnings. Skin irritants which have a potential for a heavy skin irritation should also be less suitable according to the present invention. Skin irritants which do not have a skin-irritant potential are not important with respect to wound healing, unless their presence as a filler in the cell delays the wound healing. Fillers include, for example, solids within the meaning of the present invention, such as kitchen salt, diamond dust or quartz sand.

The skin irritants can be applied to the skin surface or directly introduced into the color pigment agglomerate fragments not only in a solid form, but also in a liquid form. According to the present invention, it is particularly preferred to employ corresponding skin irritants which consist of diluted aqueous solutions, dispersions and emulsions of the skin irritants. The chemical nature of the skin irritants is not limited to a particular class of compounds. Thus, for example, diluted aqueous solutions of lactic acid, sodium hydrazine, kitchen salt, amino acids, fruit acids which optionally contain small amounts of oxidants can be employed. By simple serial experimentation, the skin-irritant potential can be established without difficulty, and thus, an appropriate choice can be made.

In addition to mechanical destruction, it is also possible, of course, to also employ the methods known in the prior art for the removal of tattoos simultaneously or shifted in time, unless the success of the treatment is not endangered thereby in an individual case.

What is claimed is:

1. A method for scarless removal of a standard tattoo from skin, consisting essentially of:
    a) pricking the skin with at least one needle, having a rough surface or sharp-edged surface, placed essentially perpendicular to the tattoo comprised of agglomerates of pigment comprising at least one of inorganic and organic color pigments present in the skin, whereby the agglomerates are mechanically destroyed by the needle prick(s); and
    b) applying skin irritants to the skin surface or introducing skin irritants into the skin where the agglomerates are present before, during or after the performance of step a) so that a scab results containing the pigment or agglomerate fragments.

2. The method according to claim 1, wherein needles having a diameter ranging from 0.001 to 0.5 mm are employed.

3. The method according to claim 1, wherein the skin irritants have a form which is selected from the group consisting of diluted aqueous solutions, dispersions and emulsions.

4. The method according to claim 1, wherein the skin irritants are selected from solids.

5. The method according to claim 1, wherein needles having a diameter ranging from 0.01 to 0.3 mm are employed.

6. The method according to claim 1, wherein the skin irritants are chemical substances selected from lactic acid, sodium hydrazine, kitchen salt, amino acids, fruit acids or oxidants.

* * * * *

(12) INTER PARTES REEXAMINATION CERTIFICATE (689th)
United States Patent
Malodobry

(10) Number: US 7,314,470 C1
(45) Certificate Issued: Sep. 16, 2013

(54) SCAR-FREE REMOVAL OF TATTOOS

(75) Inventor: Wolfgang Malodobry, Euskirchen (DE)

(73) Assignees: Barbara Simpson-Birks, Chemin de la Faience, Clemont l'Herault (FR); Richard Simpson-Birks, Chemin de la Faience, Clemont l'Herault (FR)

Reexamination Request:
No. 95/001,972, Apr. 19, 2012

Reexamination Certificate for:
Patent No.: 7,314,470
Issued: Jan. 1, 2008
Appl. No.: 10/362,594
Filed: Feb. 24, 2003

(21) Appl. No.: 95/001,972

(22) PCT Filed: Sep. 11, 2001

(86) PCT No.: PCT/EP01/10531
§ 371 (c)(1),
(2), (4) Date: Feb. 24, 2003

(87) PCT Pub. No.: WO02/36027
PCT Pub. Date: May 10, 2002

(30) Foreign Application Priority Data

| Nov. 4, 2000 | (DE) | 100 54 718 |
| Nov. 4, 2000 | (DE) | 200 18 848 U |
| Nov. 13, 2000 | (DE) | 100 56 114 |

(51) Int. Cl.
*A61B 17/50* (2006.01)

(52) U.S. Cl.
USPC .............................................. 606/131; 128/898

(58) Field of Classification Search
None
See application file for complete search history.

(56) References Cited

To view the complete listing of prior art documents cited during the proceeding for Reexamination Control Number 95/001,972, please refer to the USPTO's public Patent Application Information Retrieval (PAIR) system under the Display References tab.

*Primary Examiner* — Catherine S. Williams

(57) ABSTRACT

A method for scarless removal of a tattoo from skin which is one of human or animal skin includes pricking at least one needle through a surface of the skin essentially perpendicular thereto into the tattoo comprised of agglomerates of pigment comprising at least one of inorganic and organic color pigments present in the skin, whereby the agglomerates are mechanically destroyed; and one of applying skin irritants to the skin surface or introducing skin irritants into the agglomerates at least one of before, during or after mechanical destruction.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-6 are cancelled.

\* \* \* \* \*